(12) United States Patent
Riley

(10) Patent No.: US 8,756,836 B2
(45) Date of Patent: Jun. 24, 2014

(54) FOOT SUPPORT

(75) Inventor: Lorri A. Riley, Spearfish, SD (US)

(73) Assignee: Rylo, Inc., Spearfish, SD (US)

(*) Notice: Subject to any disclaimer, the term of this patent is extended or adjusted under 35 U.S.C. 154(b) by 673 days.

(21) Appl. No.: 13/033,477

(22) Filed: Feb. 23, 2011

(65) Prior Publication Data

US 2012/0210605 A1    Aug. 23, 2012

(51) Int. Cl.
*A61F 5/00*    (2006.01)
(52) U.S. Cl.
USPC .................................. 36/142; 36/143; 36/144
(58) Field of Classification Search
USPC ..................................................... 36/142–144
See application file for complete search history.

(56) References Cited

U.S. PATENT DOCUMENTS

| | | | |
|---|---|---|---|
| 1,958,097 A * | 5/1934 | Shaw | 36/144 |
| 2,052,115 A * | 8/1936 | Shulman | 36/144 |
| 2,616,190 A | 11/1952 | Darby | |
| 4,333,472 A | 6/1982 | Tager | |
| 4,517,981 A | 5/1985 | Santopietro et al. | |
| 4,578,882 A | 4/1986 | Talarico, II | |
| 4,747,410 A | 5/1988 | Cohen | |
| 5,327,663 A | 7/1994 | Pryce | |
| 5,345,701 A * | 9/1994 | Smith | 36/144 |
| 6,269,554 B1 * | 8/2001 | Silvestrini et al. | 36/144 |
| 6,618,960 B2 | 9/2003 | Brown | |
| 7,832,119 B2 | 11/2010 | Gilmore | |
| 8,490,301 B2 * | 7/2013 | Selner | 36/100 |
| 2005/0166423 A1 * | 8/2005 | Norton | 36/28 |
| 2006/0059726 A1 * | 3/2006 | Song et al. | 36/142 |
| 2012/0151803 A1 * | 6/2012 | Selner | 36/144 |

* cited by examiner

*Primary Examiner* — Marie Bays
(74) *Attorney, Agent, or Firm* — Stinson Leonard Street LLP

(57) ABSTRACT

A foot support for use with a human foot having a forefoot portion that supports the foot beneath the metatarsal heads and an arched midfoot portion that supports the foot beneath the metatarsal, cuneiforms, navicular, and cuboid bones and has a slope between a maximum height on the medial side of the foot support and a minimum height on the lateral side of the foot support. The foot support also includes a wedge fixed beneath the forefoot portion such that the maximum wedge height is positioned beneath the first metatarsal head and the minimum wedge height extends beneath the fourth metatarsal head. The foot support may optionally include a heel portion that supports the calcaneus and talus bones in a neutral, varus, or valgus positions.

15 Claims, 5 Drawing Sheets

FOOT SUPPORT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to a foot support for a human foot.

2. Description of Related Art

The foot comprises various ligaments, muscles, tendons, and bones that flexibly respond to shifting weight as a person walks in a normal heel to toe gait. A foot may generally be described as having a toe portion, a forefoot portion, a midfoot portion, and a heel portion. The toe portion is made up of the phalanx bones and associated ligaments, muscles, and tendons for the great or first toe (otherwise known as the hallux), second toe, third toe, fourth toe, and fifth toe. The forefoot portion is made up of the distal portion of the first through fifth metatarsal bones, also called the metatarsal heads, and the associated ligaments, muscles, and tendons. The midfoot portion is made up of the proximal portion of the first through fifth metatarsals and the cuneiforms, cuboid, and navicular bones and the associated ligaments, muscles, and tendons. The heel portion is made up of the calcaneus and talus bones and associated ligaments, muscles, and tendons. The medial longitudinal arch runs from the heel portion to the forefoot portion of the foot.

Foot flexibility allows for shock absorption and a normal foot will pronate slightly in the midfoot portion when body weight is transferred along the foot during locomotion. When the foot is too flexible it cannot properly support the body and an individual may develop pain in her foot, legs, knees, hip, back, or neck. An overly flexible foot is often caused by metatarsal-cuneiform joints that exhibit hypermobility. Between forefoot loading and heel lift, weight is transferred from the lateral aspect of the foot to the medial aspect of the foot. During this transfer, the medial longitudinal arch collapses until the metatarsal-cuneiform joints lock at the peak of their dorsiflexion. If the metatarsal-cuneiform joints are too flexible, the arch collapses more completely than it should. Over time, normal arches break down due to this continuous abuse and the individual will develop a forefoot varus deformity in one or both feet. This condition is more commonly known as "flat feet." It is estimated that 75% of the population will at some time develop foot problems, and of these individuals, 25% suffer from flat feet or pes planus.

There are varying degrees of flatfoot deformity that can occur in the legs, rearfoot, and forefoot. In a normal foot, the weight is centered on the lateral side of the heel during heel strike. Then the weight is distributed to the medial side of the foot during forefoot loading and the foot is allowed to pronate slightly, i.e., the medial longitudinal arch collapses to a certain point. During heel lift the weight is directed towards the first metatarsal head and then down the axis of the hallux at toe off. For an individual with a flat foot, the weight is distributed differently due to over-pronation and forefoot varus deformity. At heel strike the weight is more central to the heel, and then during forefoot loading, the weight is shifted immediately to the medial aspect of the foot due to the overcollapsed medial longitudinal arch. In an attempt to correct for the drastic shift in weight to the medial aspect of the foot, weight is shifted past the first metatarsal head and is concentrated at the second through fourth metatarsal heads during heel lift. At toe off, the weight is transferred to a medial aspect of the hallux. When a human foot is allowed to over-pronate in this way, more strain is placed on the ligaments, muscles, tendons, and bones of the entire body because the foot is not stable. Problems such as plantar fasciitis, bunions, shin splints, neuromas, tendonitis, and knee, hip, or back pain can occur.

Various orthotics and insoles are known in the art. Most are designed to provide comfort through cushioning. Some are designed to support feet with high arches. Others provide support for the medial longitudinal arch and are designed to prevent the talar-navicular and calcaneal-cuboid joints from exhibiting hypermobility. None of these products rebalance a foot having a forefoot varus deformity. As a result, individuals who use the orthotics and insoles known in the art to support the medial longitudinal arch in their feet, often complain that such products are uncomfortable and cause soreness in their arches.

U.S. Pat. No. 4,747,410 discloses an orthotic insert having a toe region, a forefoot region, a midfoot region, and heel cup. The insert features an anterior varus wedge that has a greater thickness at the medial side of the foot than the lateral side and a heel cup for stabilizing various components of the heel. The orthotic also features a medial shelf that is positioned to substantially underlie and support the first ray of the foot. In U.S. Pat. No. 4,333,472, a wedge is disclosed having a greater thickness at the medial side of the foot than the lateral side and positioned between the first through fifth metatarsals heads. Neither of these prior devices fully supports or rebalances a flat foot.

BRIEF SUMMARY OF THE INVENTION

The foot support of the present invention is designed to fully support a foot that over-pronates using a novel combination of components. The foot support of the present invention rebalances the foot by providing support at the metatarsal heads, along the medial longitudinal arch, and heel, while providing no support for the toes. In the preferred embodiment the foot support comprises a forefoot portion, a midfoot portion, and a heel portion. The heel portion supports the heel in a neutral position. The midfoot portion extends between the forefoot portion and the heel portion and has a sloped, longitudinal arch to support the medial longitudinal arch of the foot. The slope of the midfoot portion has a maximum height near the medial side of the foot support and a minimum height near the lateral side of the foot support. Beneath the forefoot portion there is a wedge that supports the first through fourth metatarsal heads. The wedge is shaped such that it has a maximum height positioned beneath the first metatarsal head and a minimum height position beneath the fourth metatarsal head.

In an alternative embodiment, the foot support may be incorporated into a shoe such that the insole of the shoe includes a wedged forefoot portion that supports the medial aspect of the forefoot to a greater degree than the lateral aspect of the forefoot, an arched midfoot portion that supports the medial longitudinal arch, and a heel portion that supports the heel in a neutral, varus, or valgus position. In another alternative embodiment, the foot support is truncated such that the heel portion is not included. The truncated foot support includes a wedged forefoot portion and an arched midfoot portion that support the respective portions of the foot as described above.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

Figure 1:
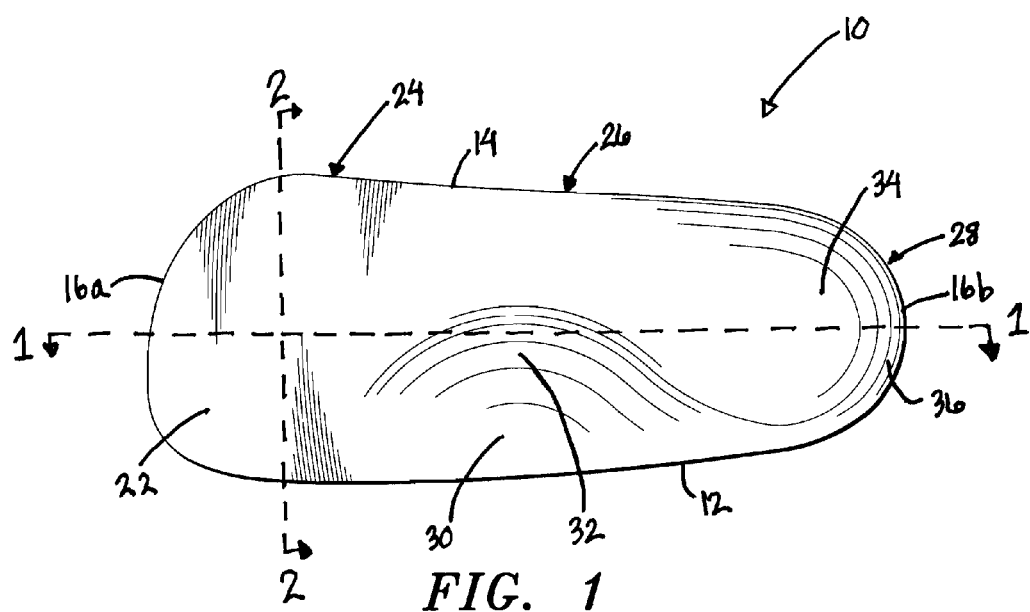
FIG. 1 shows a top view of the preferred embodiment of the foot support.
Figure 2:
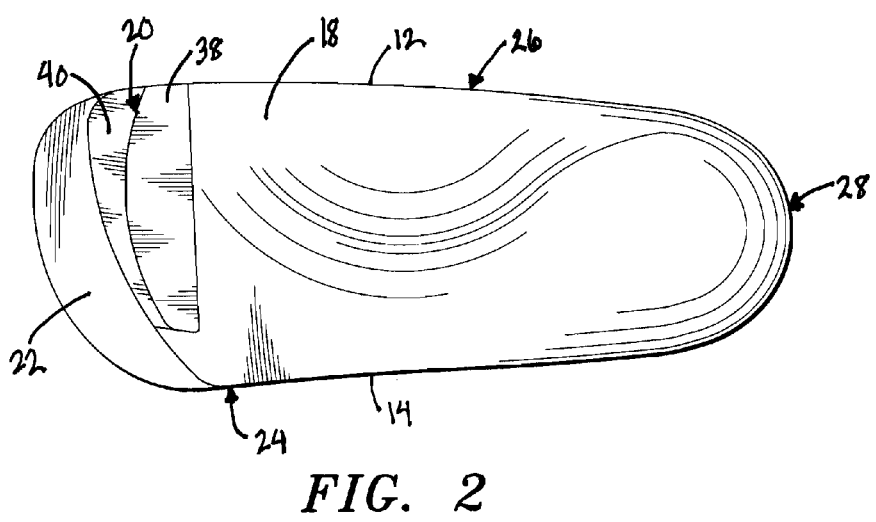
FIG. 2 shows a bottom view of the preferred embodiment of the foot support.

With reference to FIGS. 1 and 2, the foot support for a human foot 10 is shown. Foot support 10 is generally oblong shaped having a medial edge 12, a lateral edge 14, and a pair of rounded ends 16a and 16b. In the preferred embodiment, the foot support comprises insole 18, wedge 20, and cover 22. Insole 18 and cover 22 comprise forefoot portion 24, midfoot portion 26, and heel portion 28. Insole 18 is made of a rigid material capable of retaining its shape under compressive forces. Cover 22 is seamless and made of a compressible foam material. Cover 22 extends past insole 18 to provide a smooth transition from the forefoot, which is supported by forefoot portion 24 of foot support 10, to the toes, which are unsupported by foot support 10, during toe off. Midfoot portion 26 extends between forefoot portion 24 and heel portion 28 and varies in width between 30 mm and 120 mm.

Figure 3:
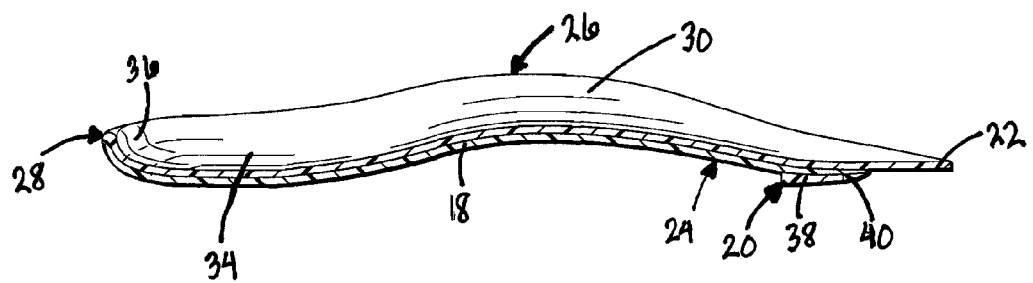
FIG. 3 shows a longitudinal cross-sectional view of the preferred embodiment of the foot support taken at line 1-1 of FIG. 1
Figure 4:
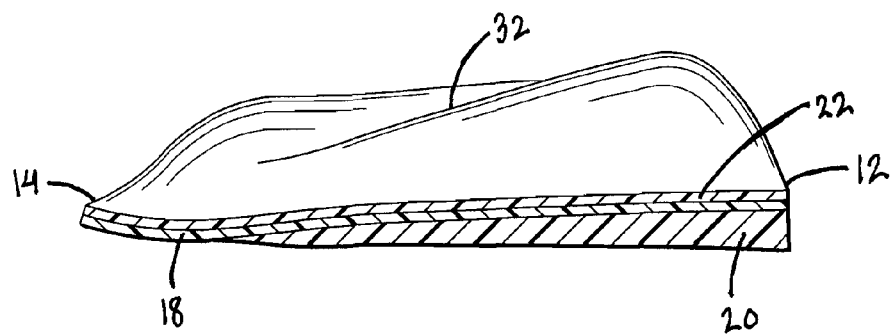
FIG. 4 shows a transverse cross-sectional view of the preferred embodiment of the foot support taken at line 2-2 of FIG. 1.

With reference to FIGS. 1 and 3, a longitudinal arch 30 begins at the distal end of heel portion 28, extends through midfoot portion 26, and terminates in forefoot portion 24. Longitudinal arch 30 has a maximum rise of about 22 mm and a run of about 135 mm. Midfoot portion 26 also has a slope 32. As shown in FIG. 4, slope 32 has a maximum height on medial edge 12 and a minimum height on the lateral side of foot support 10 but before lateral edge 14. Slope 30 has a degree of incline between 0.1 and 30 degrees, preferably between 5 and 20 degrees, and most preferably of 15 degrees.

Figure 5:
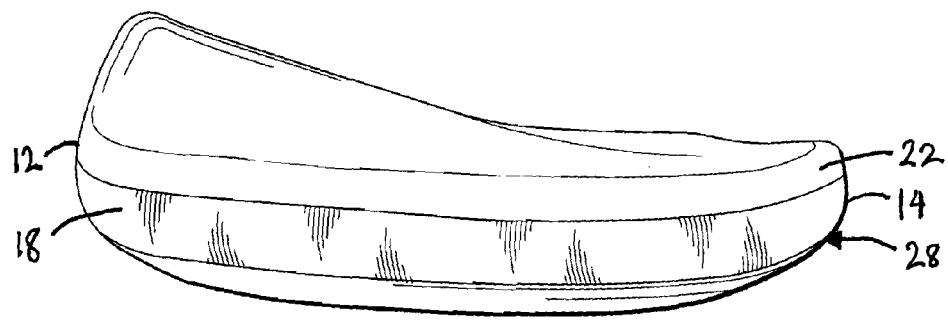
FIG. 5 shows a rear view of the preferred embodiment of the foot support.

Heel portion 28 includes a concave heel cup 34 having a heel cup wall 36 extending in a semi-circumferential manner around the sides and back of heel cup 34. Heel cup wall 36 is less than 5 cm high as measured from the center of the heel cup. With reference to FIG. 5, a neutral heel portion 28 is shown. The thickness of insole 18 at heel portion 28 on medial edge 12 is equal to the thickness of heel portion 28 on lateral edge 14. With this construction, the heel cup supports the heel in a neutral position (level).

With reference to FIG. 2, wedge 20 comprises wedge body 38 and wedge transition plane 40. Wedge 20 is fixed beneath forefoot portion 24. Wedge body 38 has a maximum height on medial edge 12 and tapers as it approaches lateral edge 14. Wedge body 38 has a degree of incline between 0.1 and 8 degrees, preferably between 1 and 4 degrees, and most preferably of 2 degrees. As shown in FIG. 3, wedge transition plane 40 tapers from wedge body 38 to the distal end of forefoot portion 24 so as to provide a smooth transition from forefoot portion 24 to cover 22. As shown in FIG. 4, the maximum height of wedge 20 is located at medial edge 12. Wedge 20 then tapers out away from medial edge 12 and stops short of lateral edge 14.

Figure 6:
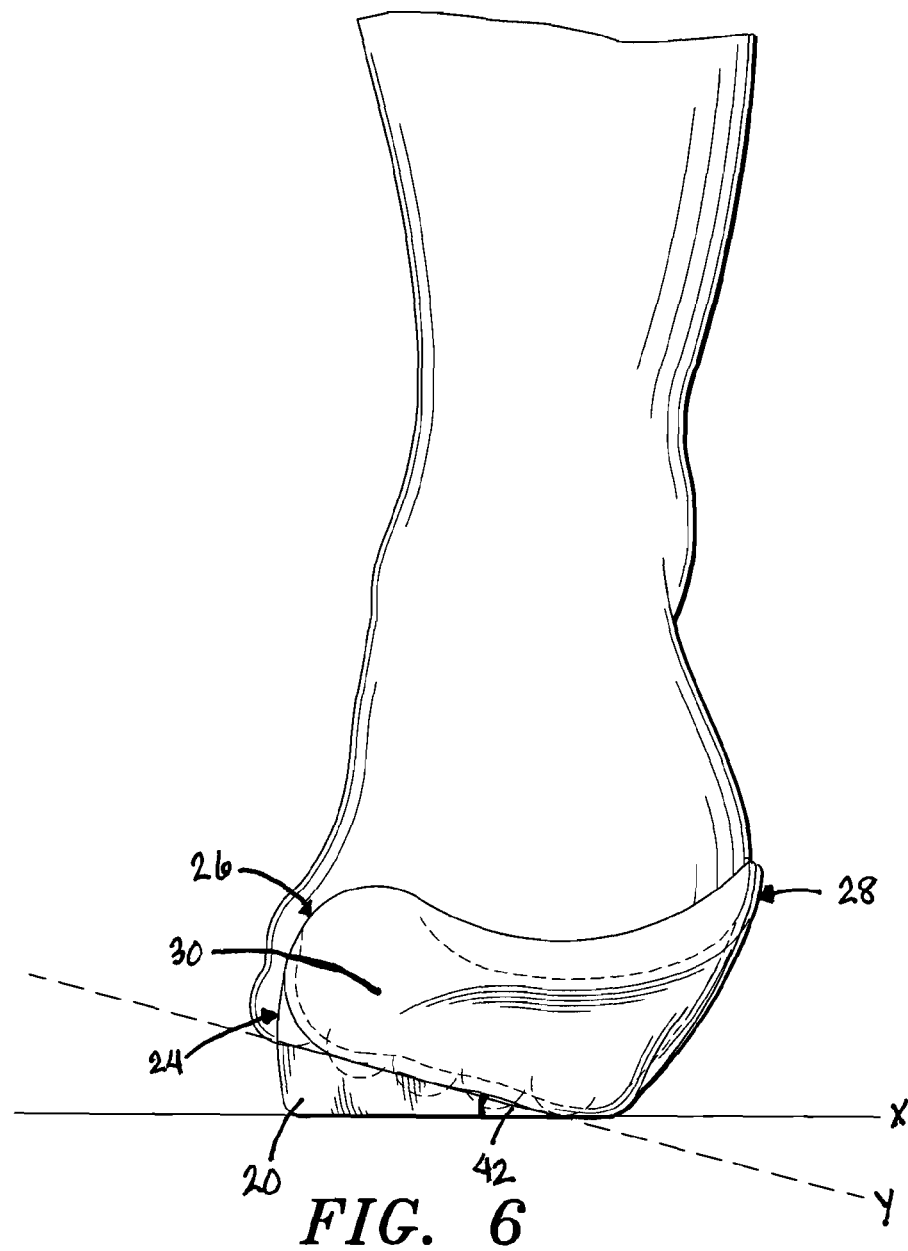
FIG. 6 shows a perspective view of the preferred embodiment of the foot support in relation to a human foot.

With reference to FIG. 6, foot support 10 is shown in use on a human foot. Heel portion 28 cups the heel and supports the calcaneus and talus bones in a neutral position. Midfoot portion 26, including longitudinal arch 30, supports the medial longitudinal arch of the foot as well as the navicular, cuboid, cuneiforms, and proximal portion of the metatarsal bones. Forefoot portion 24, including wedge 20, supports the distal portion of the metatarsal bones, otherwise known as the metatarsal heads. As shown, wedge 20 supports the first metatarsal head to a greater degree than the second metatarsal head, the second metatarsal head to a greater degree than the third metatarsal head, and the third metatarsal head to a greater degree than the fourth metatarsal head. Wedge 20 does not extend beneath the fifth metatarsal head. The degree of incline in wedge 20 is illustrated in FIG. 6 as the angle 42 between lines x and y. Angle 42 is an included angle of wedge 20. Wedge angle 42 is exaggerated in FIG. 6 for purposes of illustration. Although wedge angle 42 is approximately 15 degrees in FIG. 6, as described above, it will actually range between 0.1 and 8 degrees and most preferably will be 2 degrees. Foot support 10 is not intended to provide any significant support for the toes. When in use, support 10 rebalances a foot with a varus forefoot deformity by preventing both the medial longitudinal arch and the forefoot from collapsing beyond a normal point of collapse beneath the body weight. Wedge 20 also alleviates a portion of the pressure on the medial longitudinal arch caused by collapse of the arch onto midfoot portion 26 by supporting the metatarsal heads in the manner described above.

Variations on the preferred embodiment of foot support 10 may include some or all of the following features. The width or length of midfoot portion 26 may be increased or decreased to fit a specific style or type of shoe or foot size. The maximum height of longitudinal arch 30 may be increased or decreased and the incline of slope 32 may be increased or decreased to accommodate different degrees of forefoot varus deformities and foot flexibility. Cover 22 may be provided on any surface of foot support 10 or none at all. The material from which cover 22 is made may vary depending on its location and intended use. For example, a texturized material may be used on the bottom of foot support 10 to prevent it from slipping during use. Cover 22 may also be provided in different thicknesses to provide the desired cushion or fit in a particular area. The material for insole 18 may also vary such that foot support 10 can range from a semi-flexible to a rigid form. Suitable materials for insole 18 are, for example, foam, rubber, plastic, and cork. Also, wedge 20 and insole 18 may be combined in a single construction such that a wedged forefoot portion is provided that is capable of supporting the medial aspect of the forefoot to a greater degree than the lateral aspect of the forefoot when in use. Finally, foot support 10 may be truncated such that heel portion 28 is eliminated. This embodiment may be particularly desirable for use in sprinting spikes and other athletic shoes, women's dress shoes, and backless shoes, including sandals.

Figure 7:
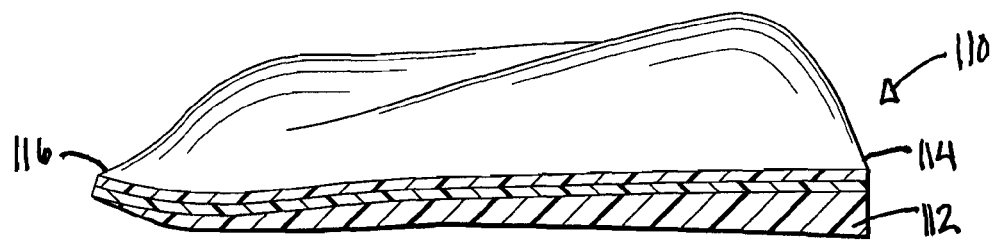
FIG. 7 shows a transverse cross-sectional view of an alternative embodiment of the foot support.

An alternative embodiment of the present invention is shown in FIG. 7 and is generally designated as foot support 110. As shown in cross-section, an elongated wedge 112 begins at medial edge 114 and extends to lateral edge 116. In this embodiment, the fifth metatarsal will be supported by wedge 112 to some degree when foot support 110 is in use.

Figure 8:
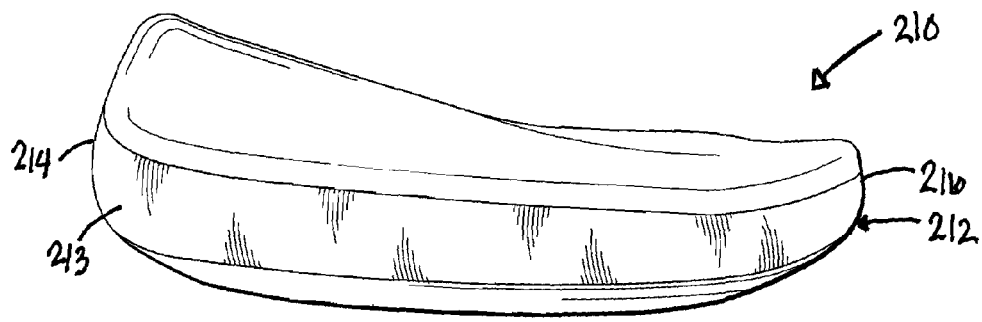
FIG. 8 shows a rear view of an alternative embodiment of the foot support.
Figure 9:
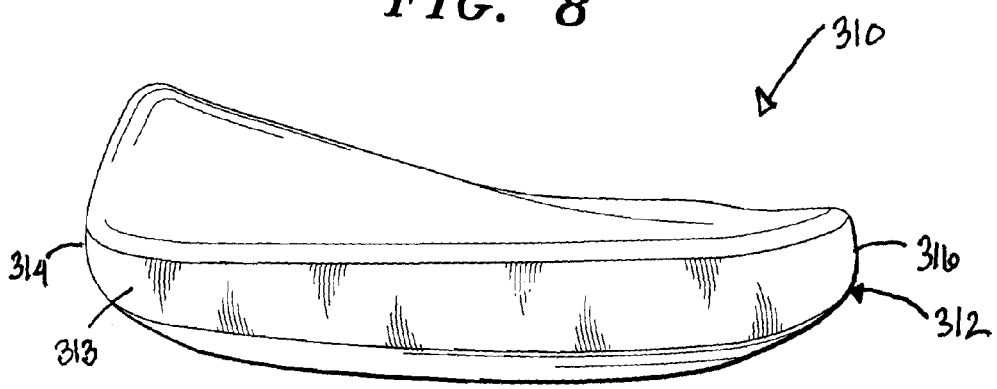
FIG. 9 shows a rear view of an alternative embodiment of the foot support.

Other alternative embodiments of the present invention are shown in FIGS. 8 and 9. As shown in FIG. 8, foot support 210 includes a varus heel portion 212. Varus heel portion 212 comprises insole 213, which has a greater thickness at medial edge 214 than at lateral edge 216 and is tapered therebetween to provide a sloped top surface. In use, varus heel portion 212 will support the medial aspect of the heel to a greater degree than the lateral aspect of the heel. As shown in FIG. 9, foot support 310 includes a valgus heel portion 312. Valgus heel portion 312 comprises sole 313, which has a greater thickness on lateral edge 316 than on medial edge 314 and tapers therebetween to provide a sloped top surface. In use, valgus heel portion 312 will support the lateral aspect of the heel to a greater degree than the medial aspect of the heel. In both the embodiments shown in FIGS. 8 and 9, the degree of incline is between 0.5 and 4 degrees, preferably between 1 and 3 degrees, and most preferable 2 degrees.

Figure 10:
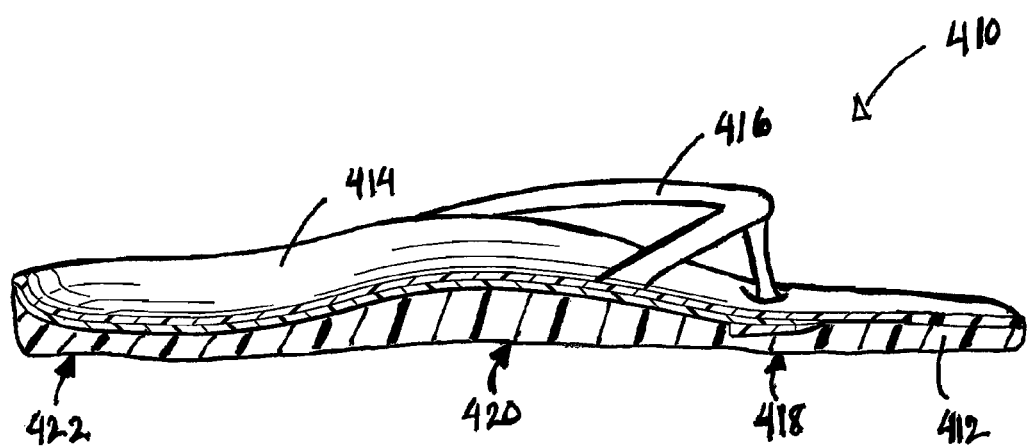
FIG. 10 shows a longitudinal cross-sectional view of an alternative embodiment where the foot support is incorporated in a shoe.

An additional alternative embodiment is shown in FIG. 10. The foot support is incorporated into shoe 410 as opposed to being a removable component. The shoe may be a sandal, dress shoe, running shoe, hiking boot, show boot, ski boot, flip-flop, sprinting spike, or any other footwear. As shown in FIG. 10, shoe 410 includes outer sole 412, insole 414, and a body 416. Body 416 comprises a system of straps but may alternatively comprise any material, mechanism, closure, or clasp known in the art for securing a shoe to a foot. Insole 414 has a wedged forefoot portion 418, an arched midfoot portion 420, and a heel portion 422. Wedged forefoot portion 418 supports the first metatarsal head to a greater degree than the second metatarsal head, the second metatarsal head to a greater degree than the third metatarsal head, and the third metatarsal head to a greater degree than the fourth metatarsal head. Alternatively, wedged forefoot portion 418 may also support the fourth metatarsal head to a greater degree than the fifth metatarsal head. As described above with reference to foot support 10, heel portion 422 may be constructed to support the heel in a neutral, varus, or valgus position. Shoe 410 supports a human foot in the same manner described above with reference to foot support 10.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A foot support for use with a human foot having a forefoot varus deformity, said foot support comprising:
   a forefoot portion configured to support a forefoot of a human foot;
   an arched midfoot portion extending from said forefoot portion and configured to support a medial longitudinal arch of the foot;
   said arched midfoot portion having a slope between a maximum height in proximity to the medial side of said arched midfoot portion and a minimum height in proximity to the lateral side of said arched midfoot portion;
   said slope of said arched midfoot portion having a degree of incline between 8 and 22 degrees;
   a wedge fixed beneath said forefoot portion, said wedge having a maximum height on the medial edge of said forefoot portion and a degree of incline between 0.1 and 8 degrees; and
   wherein said degree of incline of said wedge and said degree of incline of said slope of said arched midfoot portion are selected such that together they prevent collapse of the medial longitudinal arch and the forefoot during locomotion.

2. The foot support of claim 1, further comprising a heel portion extending from said arched midfoot portion and configured to support the calcaneus and talus bones.

3. The foot support of claim 1, wherein said wedge extends beneath a fifth metatarsal head of said foot.

4. The foot support of claim 2, further comprising a cover.

5. The foot support of claim 2, wherein said heel portion comprises an insole having a medial side of equal thickness to a lateral side, whereby said heel portion supports the calcaneus and talus bones in a neutral position.

6. The foot support of claim 2, wherein said heel portion comprises an insole having a thicker medial side as compared to a lateral side, whereby said heel portion supports the calcaneus and talus bones in a varus position.

7. The foot support of claim 2, wherein said heel portion comprises an insole having a thicker lateral side as compared to a medial side, whereby said heel portion supports the calcaneus and talus bones in a valgus position.

8. The foot support of claim 1, wherein said wedge further comprises a wedge transition plane, wherein said wedge transition plane tapers from said wedge to the distal end of said forefoot portion.

9. The foot support of claim 4, wherein said cover extends past said forefoot portion.

10. The foot support of claim 1, wherein said degree of incline of said wedge is between 1 and 4 degrees.

11. The foot support of claim 1, wherein said degree of incline of said wedge is 2 degrees.

12. The foot support of claim 1, wherein said degree of incline of said slope is between 13 and 18 degrees.

13. A shoe for use with a human foot having a forefoot varus deformity, said shoe comprising:
   a body configured to engage the foot;
   an outer sole; and
   an insole comprising a wedged forefoot portion, an arched midfoot portion, and a heel portion;
   said wedged forefoot portion having a maximum height on the medial edge of said forefoot portion and a degree of incline between 0.1 and 8 degrees;
   said arched midfoot portion having a slope between a maximum height in proximity to the medial side of said arched midfoot portion and a minimum height in proximity to the lateral side of said arched midfoot portion;
   said slope of said arched midfoot portion having a degree of incline between 8 and 22 degrees; and
   wherein said degree of incline of said wedge and said degree of incline of said slope of said arched midfoot portion are selected such that together they prevent collapse of the medial longitudinal arch and the forefoot during locomotion.

14. A foot support for use with a human foot having a forefoot varus deformity, said foot support comprising:
    means for supporting the forefoot on an incline, wherein said incline has a maximum height on the medial side of the forefoot and a degree of incline between 0.1 and 8 degrees;
    means for supporting the midfoot along a longitudinal arch, said arch having a transverse slope from a medial maximum height to a lateral minimum height and a degree of incline between 8 and 22 degrees;
    wherein said degree of incline of said wedge and said degree of incline of said slope of said arched midfoot portion are selected such that together they prevent collapse of the medial longitudinal arch and the forefoot during locomotion.

15. The foot support of claim 14, further comprising means for supporting the heel.

* * * * *